United States Patent
Burnett

(10) Patent No.: US 8,926,899 B1
(45) Date of Patent: Jan. 6, 2015

(54) PHOTOCATALYTIC DEVICES

(71) Applicant: Dust Free, LP, Royse City, TX (US)

(72) Inventor: Gregg William Burnett, Royse City, TX (US)

(73) Assignee: Dust Free, LP, Royse City, TX (US)

( * ) Notice: Subject to any disclaimer, the term of this patent is extended or adjusted under 35 U.S.C. 154(b) by 32 days.

(21) Appl. No.: 13/738,920

(22) Filed: Jan. 10, 2013

(51) Int. Cl.
  A61L 9/00    (2006.01)
  A61L 2/00    (2006.01)
  A62B 7/08    (2006.01)
  B01J 19/08   (2006.01)
  A61L 2/20    (2006.01)

(52) U.S. Cl.
  CPC ..................... *A61L 2/20* (2013.01)
  USPC . 422/24; 422/4; 422/5; 422/121; 422/186.04; 422/186.3; 422/306

(58) Field of Classification Search
  CPC ............ A61L 2/00; A61L 2/035; A61L 9/00; A61L 9/03; A61L 9/032; A61L 9/20; A61L 9/205
  USPC ............... 422/1, 4–5, 24, 121, 124, 186.04, 422/186.3, 306, 906–907
  See application file for complete search history.

(56) References Cited

U.S. PATENT DOCUMENTS

| | | | |
|---|---|---|---|
| 4,859,329 A | 8/1989 | Fink | |
| 5,011,609 A | 4/1991 | Fink | |
| 5,120,435 A | 6/1992 | Fink | |
| 5,236,585 A | 8/1993 | Fink | |
| 5,919,422 A | 7/1999 | Yamanaka et al. | |
| 6,546,883 B1 | 4/2003 | Fink et al. | |
| 6,752,970 B2 | 6/2004 | Schwartz et al. | |
| 6,784,440 B2 | 8/2004 | Fink et al. | |
| 6,949,228 B2 | 9/2005 | Ou Yang et al. | |
| 6,997,185 B2 | 2/2006 | Han et al. | |
| 7,160,566 B2 | 1/2007 | Fink et al. | |
| 7,635,659 B2 | 12/2009 | Naganuma et al. | |
| 7,871,518 B2 | 1/2011 | Ellis et al. | |
| 7,988,923 B2 | 8/2011 | Fink et al. | |
| 2003/0077211 A1 | 4/2003 | Schwartz et al. | |
| 2003/0150708 A1 | 8/2003 | Fink | |
| 2003/0230477 A1 | 12/2003 | Fink et al. | |

(Continued)

FOREIGN PATENT DOCUMENTS

| | | |
|---|---|---|
| CN | 2392106 Y | 8/2000 |
| CN | 2922905 Y | 7/2007 |

(Continued)

*Primary Examiner* — Monzer R Chorbaji
(74) *Attorney, Agent, or Firm* — Fogarty, L.L.C.

(57) ABSTRACT

Photocatalytic devices are described. In some embodiments, a photocatalytic device may include a cylindrical housing having an inlet opening and an outlet opening; one or more catalyst substrates disposed within the cylindrical housing and adapted to support a hydroxyl radical reaction with ultraviolet light and water vapor that results in hydro peroxides and hydroxyl ions; an ultraviolet light source disposed within the cylindrical housing and adapted to provide the ultraviolet light to the one or more catalyst substrates; and a fan disposed within the cylindrical housing and adapted to cause air to enter the cylindrical housing via the inlet opening, circulate through the one or more catalyst substrates within the cylindrical housing, and exit the cylindrical housing via the outlet opening. The catalyst substrates comprising a hydrated multimetallic catalyst having two or more elements selected from the group: Titanium dioxide, Platinum, Gold, Silver, Copper, Rhodium, Ruthenium, Lanthanum, Carbon and Fluoride.

20 Claims, 6 Drawing Sheets

(56) References Cited

U.S. PATENT DOCUMENTS

| | | |
|---|---|---|
| 2004/0016887 A1 | 1/2004 | Fink et al. |
| 2004/0056201 A1 | 3/2004 | Fink et al. |
| 2004/0156959 A1 | 8/2004 | Fink et al. |
| 2004/0166037 A1* | 8/2004 | Youdell et al. ............ 422/186.3 |
| 2004/0197243 A1 | 10/2004 | Schwartz et al. |
| 2005/0186124 A1 | 8/2005 | Fink et al. |
| 2006/0144690 A1 | 7/2006 | Fink et al. |
| 2006/0163135 A1 | 7/2006 | Ellis et al. |
| 2006/0228275 A1 | 10/2006 | Rutman et al. |
| 2006/0266221 A1 | 11/2006 | Fink et al. |
| 2007/0110860 A1 | 5/2007 | Fink et al. |
| 2009/0183943 A1 | 7/2009 | Leistner et al. |
| 2009/0217690 A1 | 9/2009 | Silderhuis |
| 2011/0033346 A1* | 2/2011 | Bohlen et al. ............ 422/186.3 |
| 2011/0250125 A1 | 10/2011 | Fink et al. |

FOREIGN PATENT DOCUMENTS

| | | |
|---|---|---|
| CN | 101245939 A | 8/2008 |
| CN | 201135626 Y | 10/2008 |
| DE | 20211178 U1 | 11/2002 |
| WO | WO 2006/134149 A1 | 12/2006 |

* cited by examiner

PHOTOCATALYTIC DEVICES

TECHNICAL FIELD

Embodiments of the invention are directed, in general, to oxidation technology for air purification systems and, more specifically, to photocatalytic devices.

BACKGROUND

Ultraviolet (UV) light represents the frequency of light between 185 nanometers (nm) and 400 nm, and it is invisible to the naked eye. There are three distinct bands of light within the UV spectrum: UV-A, UV-B, and UV-C. Longwave UV light (315 nm to 400 nm) or UV-A refers to what is commonly called "black light." UV-B (280 nm to 315 nm) or midrange UV is the type of light that causes sunburn. Germicidal UV light (185 nm to 280 nm) or UV-C is effective in microbial control. For example, research has demonstrated that UV light between 254 nm and 265 nm can be very efficient in the destruction of various microbials and other microorganisms.

A photocatalytic air purifier is based on photocatalytic oxidation (PCO), a technology that converts fine particles and/or toxic gasses into safer compounds. Generally speaking, a photocatalytic air cleaner may use broad-spectrum, ultraviolet light, which reacts with a chemical catalyst (e.g., thin-film titanium dioxide-based material) to oxidize organic compounds, thus reducing or eliminating certain microorganisms otherwise present in the air.

SUMMARY

This Summary is provided to introduce certain concepts in a simplified form that are further described below in the Detailed Description. This Summary is not intended to identify key features or essential features of the claimed subject matter, nor is it intended to be used to limit the scope of the claimed subject matter.

In an illustrative, non-limiting embodiment, a photocatalytic device may include a cylindrical housing having an inlet opening and an outlet opening; one or more catalyst substrates disposed within the cylindrical housing and adapted to support a hydroxyl radical reaction with ultraviolet light and water vapor that results in hydro peroxides and hydroxyl ions; an ultraviolet light source disposed within the cylindrical housing and adapted to provide the ultraviolet light to the one or more catalyst substrates; and a fan disposed within the cylindrical housing and adapted to cause air to enter the cylindrical housing via the inlet opening, circulate through the one or more catalyst substrates within the cylindrical housing, and exit the cylindrical housing via the outlet opening.

For example, the one or more catalyst substrates may include a hydrated quad-metallic catalyst. The photocatalytic device may also include a diffuser coupled to the cylindrical housing and adapted to spread the air exiting the cylindrical housing via the outlet opening and/or a power supply coupled to the cylindrical housing and adapted to provide power to the ultraviolet light source and to the fan.

In some implementations, the photocatalytic device may be configured to operate in an upright position. Additionally or alternatively, the photocatalytic device may be configured to operate in a horizontal position.

In some embodiments, the photocatalytic device may include one or more reflectors disposed within the cylindrical housing and positioned adjacent to the one or more catalyst substrates, the one or more reflectors having a shape configured to distribute reflected ultraviolet light from the ultraviolet light source across a surface of the one or more catalyst substrates. In some cases, each of the one or more reflectors may have a curved edge. In other cases, each of the one or more reflectors may have one or more straight edges.

In some implementations, the shape of the one or more reflectors may be configured to minimize a distance between the ultraviolet light source and a near surface of the one or more catalyst substrates. In other implementations, the shape of the one or more reflectors may be configured to minimize a distance between the ultraviolet light source and a far surface of the one or more catalyst substrates. Also, the one or more catalyst substrates may comprise a cylindrical catalyst substrate.

In another illustrative, non-limiting embodiment, a method may include causing air to enter a cylindrical housing of a photocatalytic device via an inlet opening, circulate through one or more catalyst substrates within the cylindrical housing, and exit the cylindrical housing via an outlet opening, the one or more catalyst substrates adapted to support a hydroxyl radical reaction with ultraviolet light and water vapor that results in hydro peroxides and hydroxyl ions within the photocatalytic device, the ultraviolet light provided by an ultraviolet light source disposed within the cylindrical housing.

In some cases, causing the air to enter the cylindrical housing, circulate through the one or more catalyst substrates, and exit the cylindrical housing, may include powering a fan. Additionally or alternatively, causing the air to exit the cylindrical housing may include outputting the air through a diffuser adapted to spread the air at the outlet opening.

In some implementations, the method may include reflecting the ultraviolet light by one or more convex reflectors disposed within the cylindrical housing and positioned adjacent to the one or more catalyst substrates. The shape of the one or more convex reflectors may be configured to minimize a distance between the ultraviolet light source and a near surface of the one or more catalyst substrates. Additionally or alternatively, the shape of the one or more convex reflectors may be configured to minimize a distance between the ultraviolet light source and a far surface of the one or more catalyst substrates.

In yet another illustrative, non-limiting embodiment, a method may include providing a cylindrical housing having an inlet opening and an outlet opening; assembling one or more catalyst substrates within the cylindrical housing and adapted to support a hydroxyl radical reaction with ultraviolet light and water vapor that results in hydro peroxides and hydroxyl ions; assembling an ultraviolet light source within the cylindrical housing and adapted to provide the ultraviolet light to the one or more catalyst substrates; positioning one or more convex reflectors within the cylindrical housing and adjacent to the one or more catalyst substrates; and assembling a fan within the cylindrical housing and adapted to cause air to enter the cylindrical housing via the inlet opening, circulate through the one or more catalyst substrates within the cylindrical housing, and exit the cylindrical housing via the outlet opening. The method may also include providing a power supply coupled to the ultraviolet light source and to the fan.

BRIEF DESCRIPTION OF THE DRAWINGS

Figure 1:
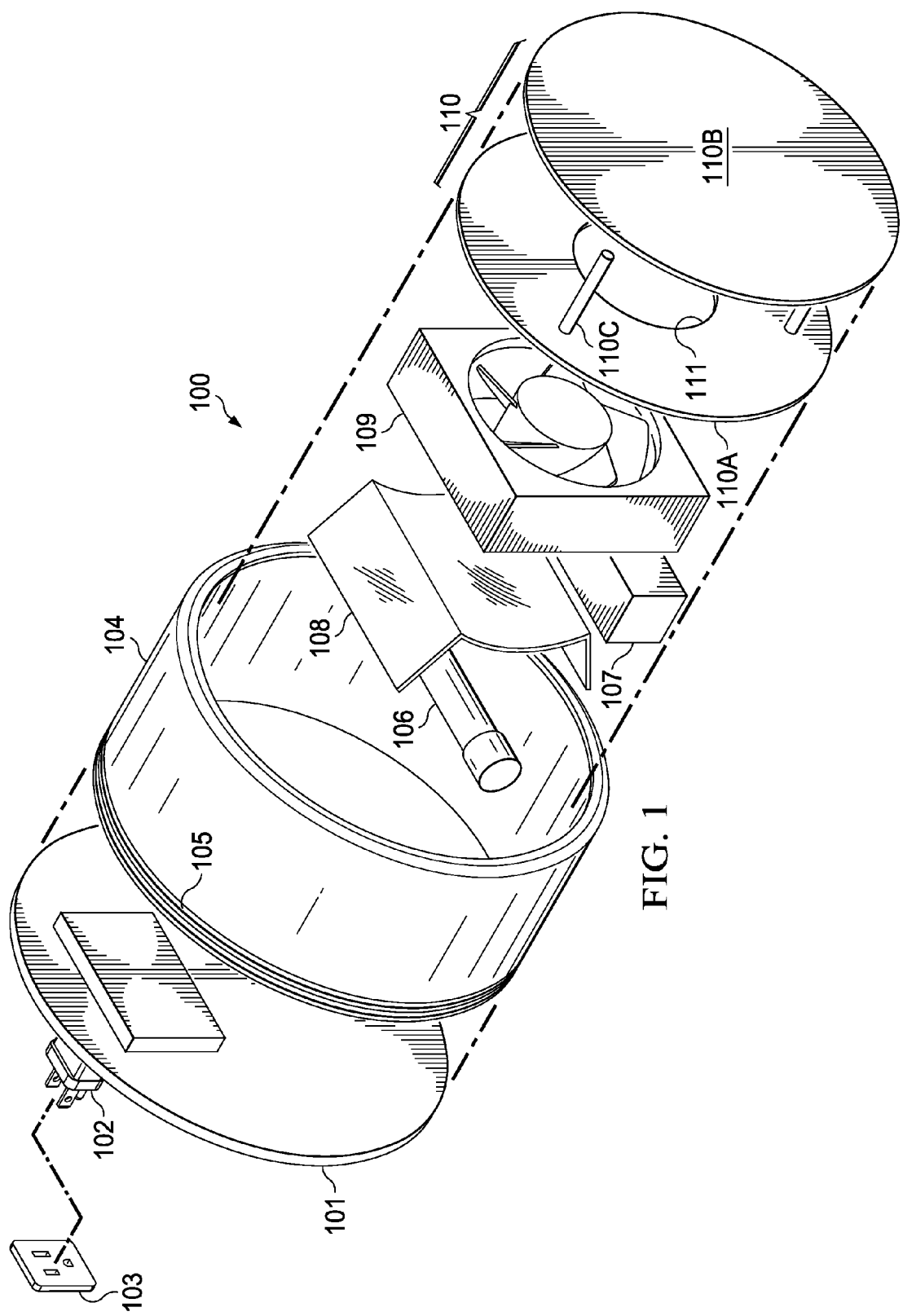

Having thus described the invention in general terms, reference will now be made to the accompanying drawings, which are not necessarily drawn to scale, and wherein:

FIG. 1 is an exploded view of a photocatalytic device according to some embodiments.

Figure 2:
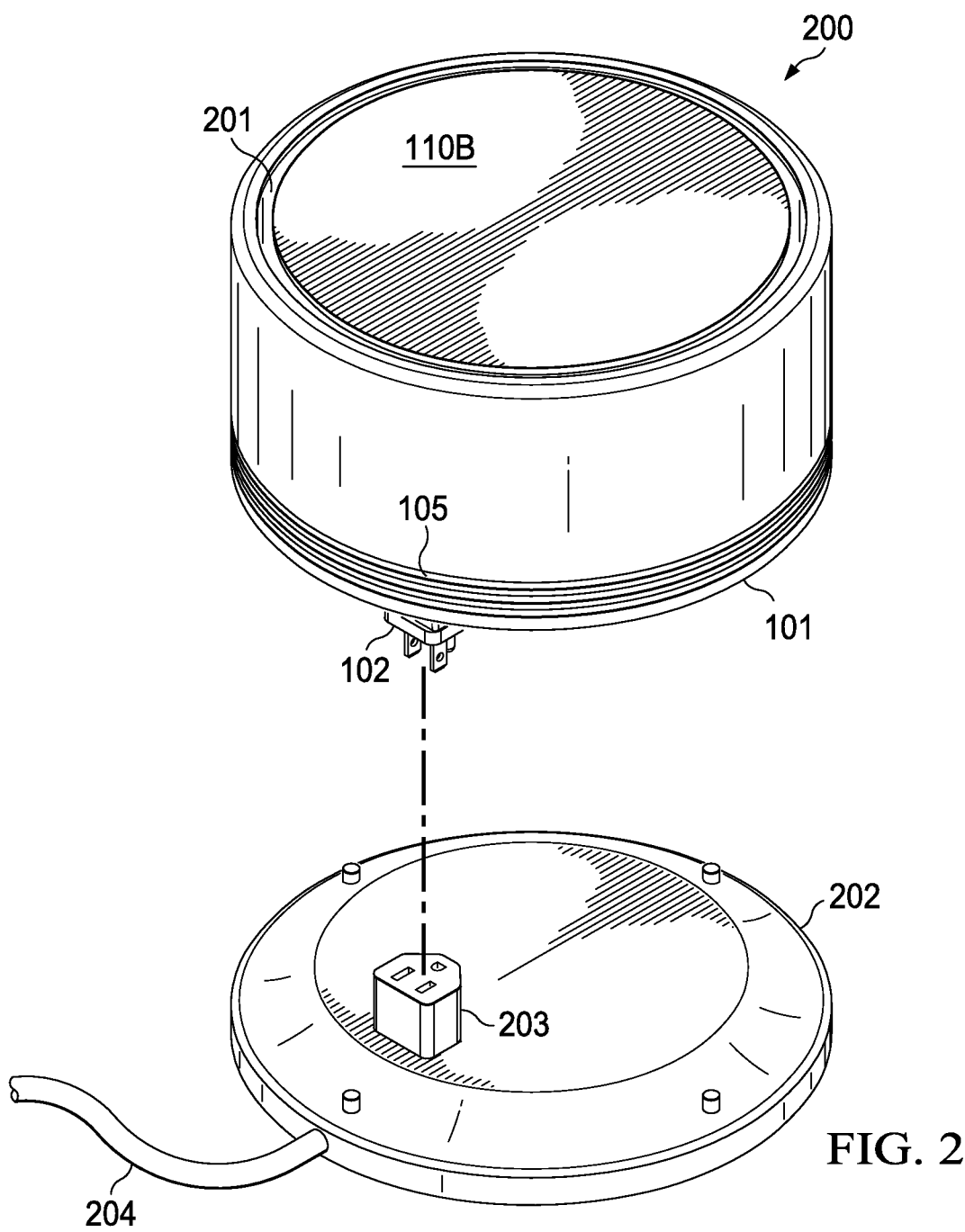

FIG. 2 is a diagram illustrating an assembled photocatalytic device according to some embodiments.

Figure 3:
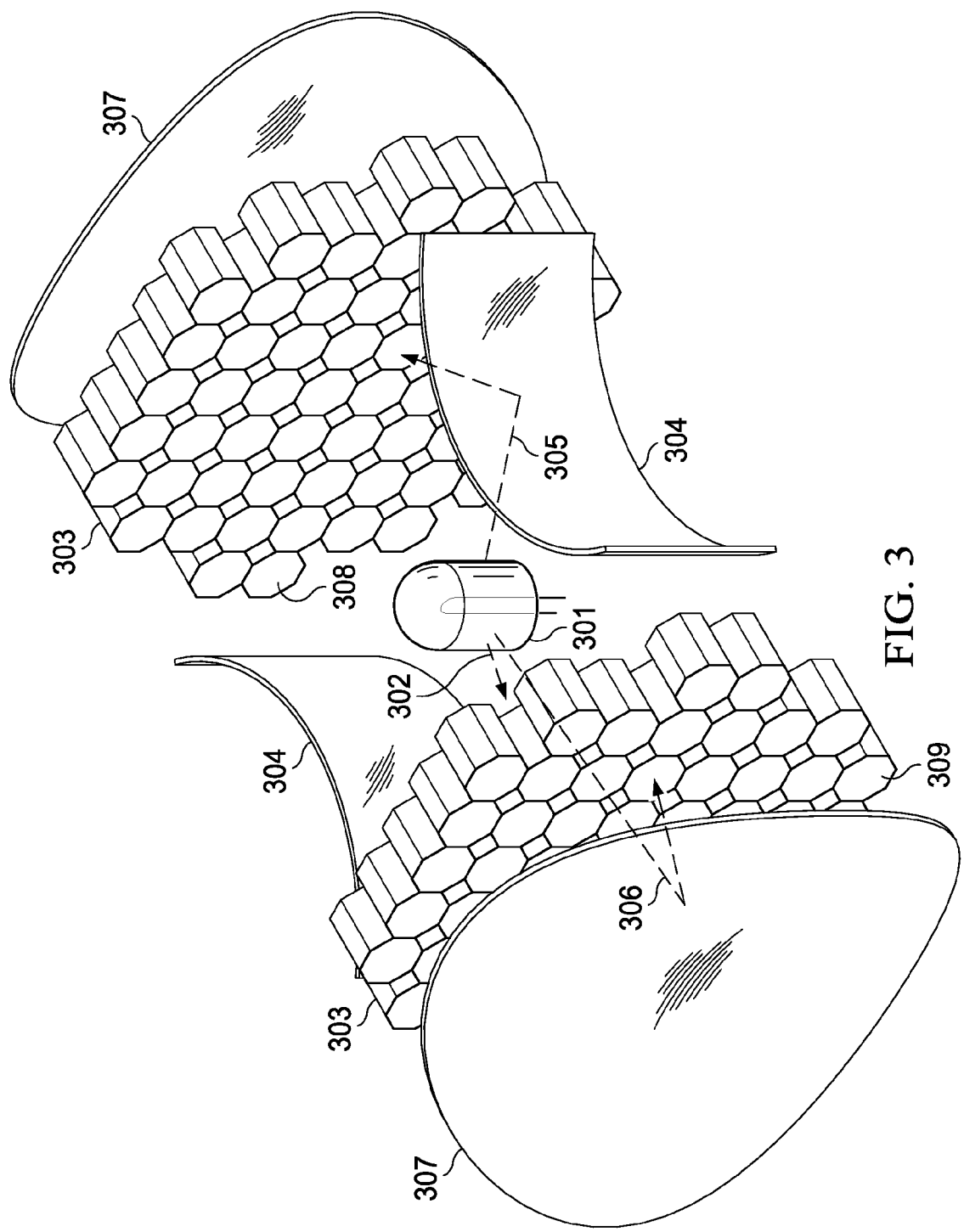

FIG. 3 is a block diagram illustrating elements of a photocatalytic device according to some embodiments.

Figure 4:
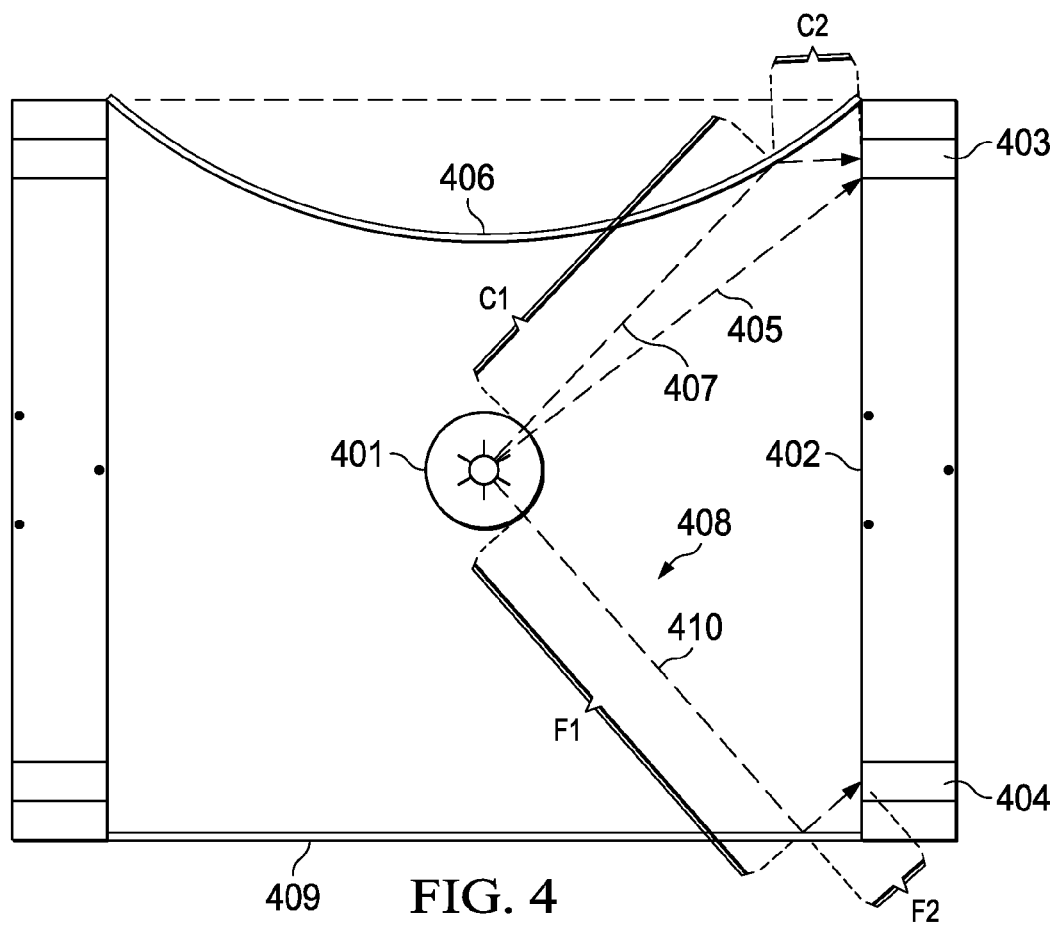

FIG. 4 is a block diagram illustrating the operation of a curved reflector according to some embodiments.

Figure 5:
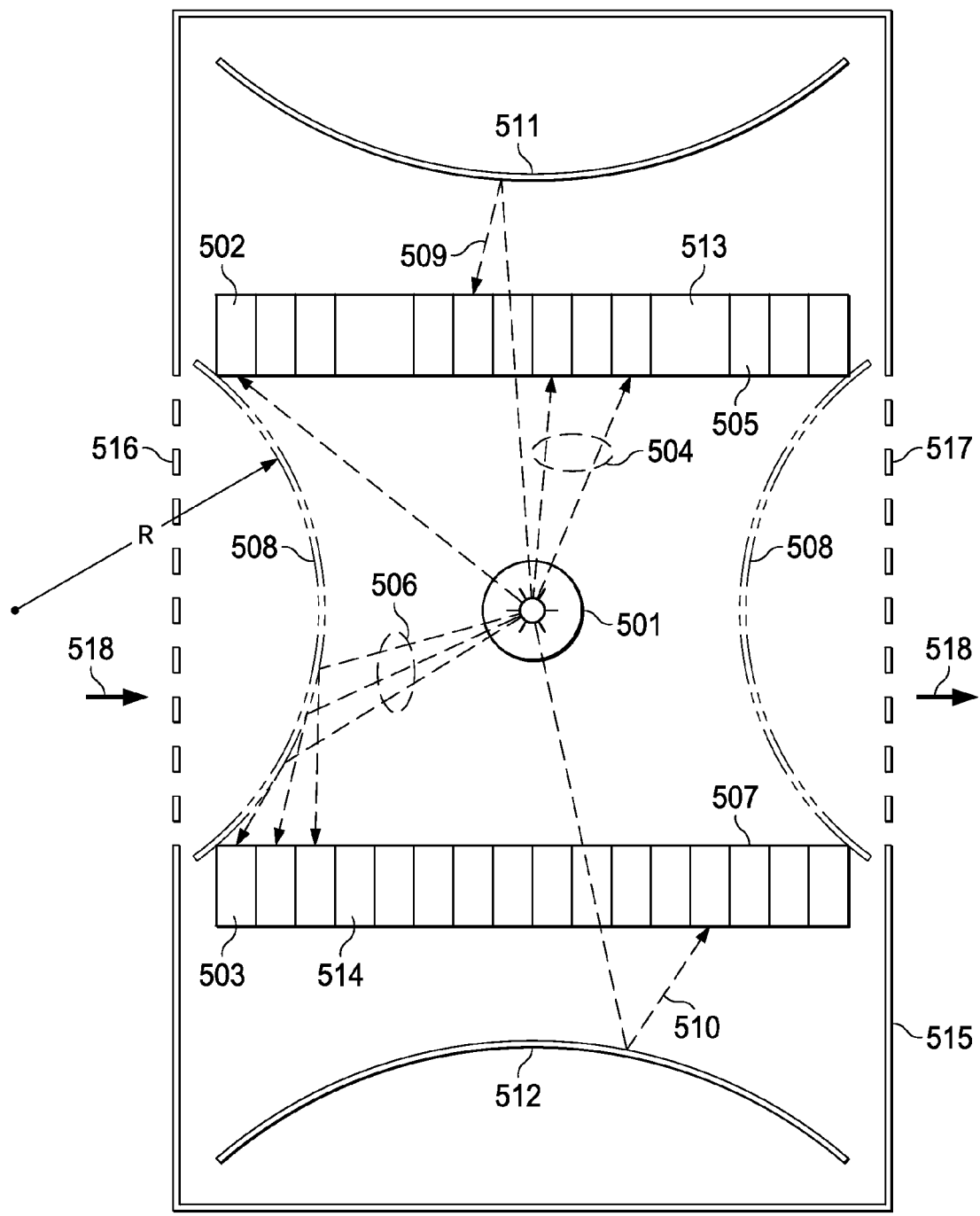

FIG. 5 is a block diagram illustrating the illumination of opposed surfaces of a target structure according to some embodiments.

Figure 6:
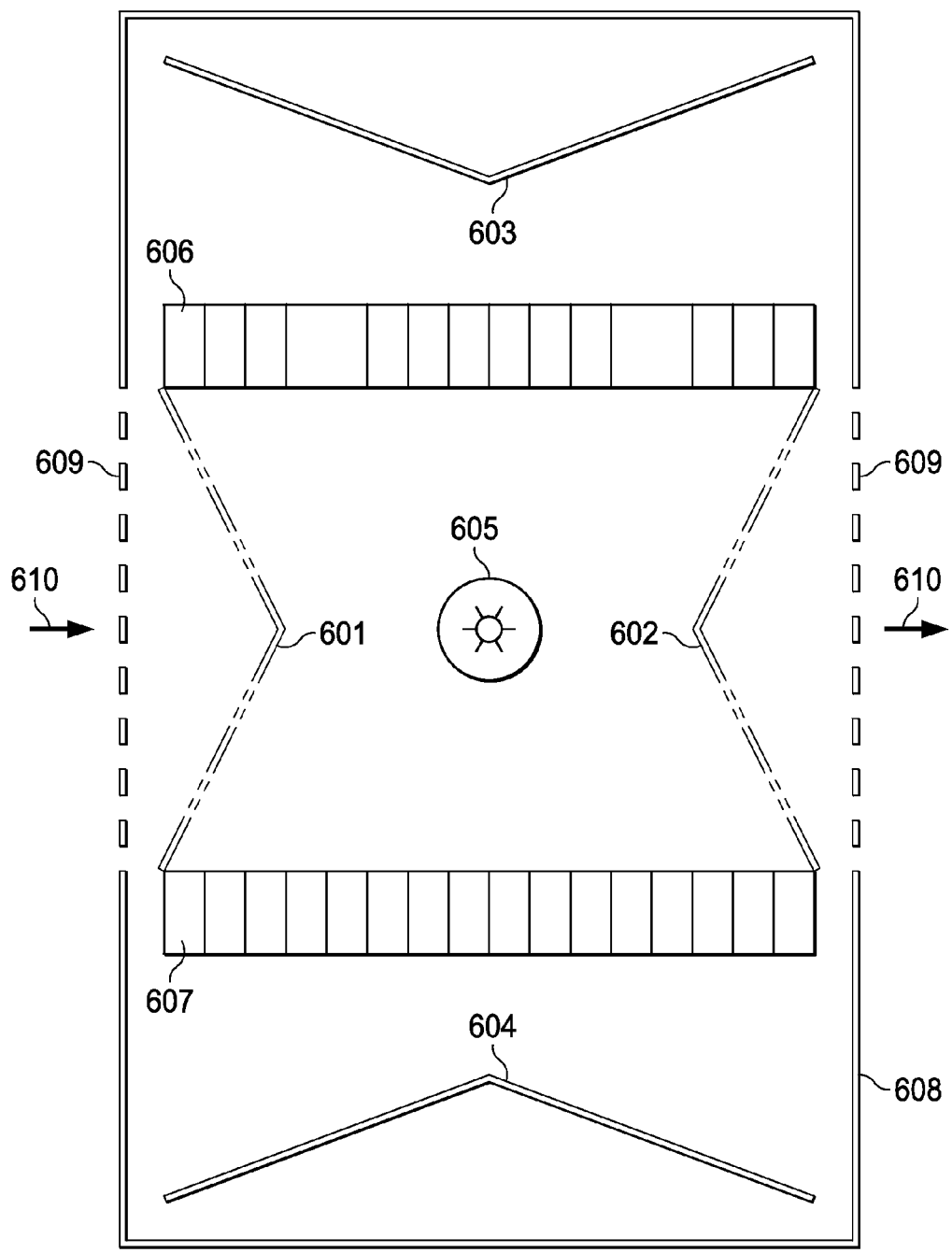

FIG. 6 is a block diagram illustrating another photocatalytic device according to some embodiments.

DETAILED DESCRIPTION

Turning to FIG. 1, an exploded view of photocatalytic device 100 according to some embodiments. As illustrated, photocatalytic device 100 may include plate 101, upon which electrical element(s) 102 may be mounted. For example, for example, electrical element(s) 102 may include a plug configured to be coupled to a standard electrical outlet and/or it may include one or more voltage regulators and/or converters configured to obtain electrical power from outlet 103 (or from a battery) and to provide it to one or more of device 100's internal components. Housing or enclosure 104 (e.g., a cylindrical or approximately cylindrical housing) may be mounted onto plate 101, and may include one or more inlet openings 105 (e.g., a grill, a vent, etc.). Internal components assembled within housing 104 may include ultraviolet light source 106, one or more photocatalytic structures 107, one or more reflectors 108, and fan 109. The arrangement and inter-relationship of these components may vary in different embodiments. Generally, ultraviolet light from source 106 shines on photocatalytic structure(s) 107 either directly or after reflection off of reflector(s) 108.

Diffuser assembly 110 may be coupled to housing 104 and may be adapted to spread or distribute the air exiting housing 104 via outlet opening 111. For example, diffuser 110 may include two or more plates, inner plate 110A having outlet opening 111 and an outer plate 100B. As illustrated, the two or more plates may be coupled to each other via one or more columns 110C that provide spacing between these elements. In other embodiments, however, outer plate 100B may be flat and/or configured to allow additional photocatalytic device(s) similar to device 100 to be stacked or mounted upon device 100, thereby increasing the collective air processing capacity of the system.

In operation, photocatalytic device 100 may be used in an upright (on a flat surface, vertical stand, etc.) or horizontal position (plugged directly into and supported by outlet 103, horizontal stand, etc.). When powered (e.g., via outlet 103, a battery, etc.), fan 109 may cause air to enter housing 104 via inlet opening 105, circulate through one or more catalyst substrates 107, and exit housing 104 via an outlet opening 111. Ultraviolet light may be provided by ultraviolet light source 106, and catalyst substrates 107 may be adapted to support a hydroxyl radical reaction with the ultraviolet light and water vapor that results in hydro peroxides and hydroxyl ions within photocatalytic device 100. These hydro peroxides and hydroxyl ions are circulated into the local environment by the air flowing through housing 104.

In some embodiments, one or more of plate 101, housing 104, and/or diffuser 110 may be built with a thermoplastic material such as, for example, polyethylene, polypropylene, polystyrene, polyvinyl chloride, polytetrafluoroethylene (PTFE), etc. Additionally or alternatively, these elements may be built with thermosetting polymers or the like. In other embodiments, one or more of plate 101, housing 104, and/or diffuser 110 may be built with a metal or metal alloy material.

FIG. 2 is a diagram illustrating an assembled photocatalytic device according to some embodiments. Particularly, photocatalytic device 200 in an upright configuration is shown with built-in electrical connector 102 operable to be connected to plug 203 of base 202. In some embodiments, electrical cord 204 may provide power to connector 102 via plug 203. For example, base 202 may include one or more power supply elements (e.g., voltage regulators and/or converters). Additionally or alternatively, device 200 may be battery-operated and base 202 may include an electrical or rechargeable battery.

Internal components including ultraviolet light source 106, one or more photocatalytic structures 107, one or more reflectors 108, and fan 109 are enclosed by housing 104. As previously described, air may enter housing 104 through inlet opening 105 and it may exit housing 104 through outlet opening 111, thus dispersed via exit point 201, which is located around the perimeter of device 200 between housing 104 and outer plate 110B.

FIG. 3 is a block diagram illustrating elements of a photocatalytic device according to some embodiments. An ultraviolet light source 301 generates ultraviolet light 302. One or more photocatalytic structures 303 are positioned near ultraviolet light source 301 and are illuminated by the ultraviolet light 302. In an embodiment, the photocatalytic structures 303 may include a plurality of fluted structures arranged in a honeycomb formation.

Photocatalytic structures 303 may be, for example, a hydrated catalytic matrix. When ultraviolet light 302 impacts the photocatalytic structures 303, ozone is produced in the catalytic matrix. The catalyst may support a hydroxyl radical reaction with water vapor that results in hydro peroxides, hydroxyl ions, super oxide ions, passive negative ions hydroxides, and ozonide ions. These are highly reactive chemical species. The hydroxyl radicals are very strong oxidizers and will attack organic materials. This creates oxidation that helps to reduce odors, volatile organic compounds (VOCs), airborne viruses, bacteria, mold and/or other types of air pollution. The hydrated catalytic matrix may comprise any catalytic compound, element or combination thereof. In one embodiment, the hydrated catalytic matrix may be a hydrated multi-metallic catalyst multi-metallic catalytic matrix. One such multi-metallic catalytic matrix may be a multi-metallic catalytic matrix comprising one or more of: Titanium dioxide, Platinum, Gold, Silver, Copper, Rhodium, Ruthenium, and Lanthanum, for example. Additional elements, such as Carbon and/or Fluoride, may also be included in the catalytic matrix. In other embodiments, different combinations of rare and noble metals may be used for the catalytic matrix in various combinations.

Titanium dioxide is a well-known photocatalyst for water and air treatment as well as for catalytic production of gases. For example, Titanium dioxide has been extensively studied as a photocatalyst for the remediation of contaminated water because it is highly active under UV irradiation, stable, non-toxic, and inexpensive. The properties of Titanium dioxide, such as surface area, surface charge, crystallinity, surface crystalline plane, particle size, density of surface functional groups, and lattice defects, influence the photocatalytic activities in a complex way. The surface property of Titanium dioxide is particularly important in determining the photocatalytic reaction kinetics, mechanisms, and efficiencies because the photocatalytic reactions mostly take place on the surface. The surface modification of Titanium dioxide has been tried in various ways which include polymer coating, metal deposition, anion complexation, and hybridization with silica. Such modifications of the Titanium dioxide surface enhance the photocatalytic efficiencies, change the reaction mechanisms, or alter the distribution of intermediates and products.

Each surface modification method has its unique role in affecting the kinetics and mechanisms of photocatalytic reactions. The Platinization of Titanium dioxide (e.g., Pt/TiO$_2$) has been established as a popular surface modification technique because exhibits enhanced activities for many photocatalytic reactions. It is believed that Platinum deposits on Titanium dioxide attract and hold electrons with retarding their recombination with holes. It has been reported that Titanium dioxide modified with both Fluoride and Platinum (e.g., F—TiO2/Pt) exhibits a unique photocatalytic activity for the anoxic degradation of phenolic compounds and the H$_2$ production accompanied by the degradation of phenolic compounds. Other elements, such as Carbon, may also be used in the photocatalytic structures.

The general scheme for the photocatalytic destruction of organics begins with its excitation by supra-band-gap photons, and continues through redox reactions where OH radicals, formed on the photocatalyst surface, play a major role. The presence of Gold and Platinum in the vicinity of Titanium dioxide has been observed to improve the performance of the photocatalyst. This effect has been attributed to a better charge separation between the photo-induced charge carriers and to an ability of the metal to prevent the deactivation of the photocatalyst, probably by a spillover mechanism that supplies oxygen to the Titanium dioxide surface. In addition to Platinum, other metallic elements may be used as catalysts either alone or in combination with other elements. For example, Ruthenium and Lanthanum may also be used as catalysts alone or in combination with other metals.

Embodiments of the photocatalytic structures disclosed herein will be understood to include any one or any combination of two or more of the above referenced elements in a hydrated catalytic matrix. For example, a multi-metallic catalytic matrix may comprise one or more of: Titanium dioxide, Platinum, Gold, Silver, Copper, Rhodium, Ruthenium, and Lanthanum. Additional elements, such as Carbon and/or Fluoride, may also be included in the catalytic matrix. In one embodiment, the catalytic matrix is a hydrated quad-metallic catalyst comprising four or more of the above listed elements (not necessarily all metals). In another embodiment, the catalytic matrix is a hydrated quintuple-metallic catalyst comprising five or more of the above listed elements. Additional embodiments comprise higher order-metallic catalysts (e.g., sextuple-metallic, septuple-metallic, etc.).

Ultraviolet light source 301 may be, for example, a high-intensity, broad-spectrum ultraviolet bulb or tube. In other embodiments, the ultraviolet source may be a low pressure fluorescent quartz bulb or a medium pressure amalgam lamp. Ultraviolet light falls in the band of light between 185 nm and 400 nm. There are three distinct bands of light within the ultraviolet spectrum: UV-A, UV-B, and UV-C. Longwave UV light (315 nm to 400 nm), or UV-A, refers to what is commonly called "black light." Midrange UV (280 nm to 315 nm), or UV-B, causes sunburn. Germicidal UV light (185 nm to 280 nm), or UV-C, is effective in microbial control. Research has demonstrated that the most efficient frequency for microbial destruction is between 254 nm and 265 nm within the UV-C band. Germicidal lamps that produce the majority of their output in this range have proven to be effective in microbial control/destruction.

One or more curved reflectors 304 are positioned to reflect ultraviolet light 305 from ultraviolet light source 301 to the face 308 of photocatalytic structures 303. As a result, photocatalytic structures 303 receive both direct ultraviolet light from source 301 and reflected ultraviolet light 305 from curved reflectors 304.

Some ultraviolet light 306 passes through photocatalytic structures 303. Additional curved reflectors 307 are positioned so that ultraviolet light 306 is reflected back to photocatalytic structures 303 on the face 309 opposite ultraviolet light source 301.

In an embodiment, reflectors 306 and 307 are curved in a manner that increases and/or optimizes the distribution of ultraviolet light across the faces 308 and 309 of photocatalytic structures 303.

FIG. 4 is a block diagram illustrating the operation of a curved reflector according to some embodiments. The inverse-square law of light results in a rapid drop-off in the intensity of ultraviolet light as it is radiated away from the light source. The intensity of light waves radiating from a light source is inversely proportional to the square of the distance from the light source. This affects the amount of energy provided to surfaces that are illuminated by the light source. For example, a far surface that is twice as far away from a light source as a near surface, receives only one-quarter of the energy that is received by the near surface. Accordingly, it is important to reduce and/or minimize the distance traveled by the ultraviolet light within the photocatalytic device.

Light source 401 that broadcasts light on target surface 402, which includes a plurality of segments 403, 404. Segment 403 receives light directly from source 401, as illustrated by ray 405. Segment 403 also receives light indirectly from source 401 after reflection from curved reflector 406, as illustrated by ray 407. Light 407 reflected off of curved reflector 406 has a total distance C1+C2.

Segment 404 receives light directly from source 401, as illustrated by ray 408. Segment 404 also receives light indirectly from source 401 after reflection from flat reflector 409, as illustrated by ray 410. The light 410 reflected off of flat reflector 409 has a total distance F1+F2. As illustrated in FIG. 4, the distance traveled by ray 410 is longer than the distance traveled by ray 407. Therefore, the ray 407 from curved reflector 406 will have a higher intensity and higher energy level when it reaches segment 403 when compared to the intensity and energy level of ray 410 when it reaches segment 404.

In addition to reducing and/or minimizing the distance traveled by ray 407, curved reflector 406 may also cause the reflected ray to impact the target surface 402 in a perpendicular or nearly perpendicular direction. On the other hand, ray 410 reflected off of flat reflector 409 impacts the target surface 402 at an acute angle. Where segments 403, 404 are hollow structures, such as fluted segments of a honeycomb substrate, the perpendicular rays 407 better illuminates the interior of the segment 403 compared to ray 410's illumination of segment 404.

FIG. 5 is a block diagram illustrating the illumination of opposed surfaces of a target structure according to some embodiments. Ultraviolet light source 501 generates broadband ultraviolet light that illuminates target structures 502, 503. Ultraviolet light rays 504 impact a near side 505 of target structure 502. Reflected rays 506 also impact the near side 507 of target structure 503. Reflective surface 508 is shaped to optimize the impact of reflected rays 506 against near surface 507. The curvature R of reflective surface 508 is selected so that reflected rays 506 travel an optimized minimum distance between source 501 and surface 507.

The curvature R of reflective surface 508 may be of a constant radius, such as in a cross-section of a cylindrical surface. In other embodiments, the curvature R of reflective surface 508 may have a variable radius, such as in a cross-section of a paraboloid or ellipsoid. In yet other embodiments, the curvature of reflective surface 508 has a radius that varies both in a vertical and horizontal direction.

Some ultraviolet light, such as rays 509, 510, may pass through target structures 502, 503 when those structures are comprised of hollow segments. Reflective surfaces 511, 512 reflect rays 509, 510 back against the far surface 513, 514 of the target structures 502, 503. Reflective surfaces 511, 512 are shaped to optimize the impact of reflected rays 509, 510 against near surface 507. Like surface 508, the curvature of reflective surfaces 511, 512 are selected so that reflected rays 509, 510 travel an optimized minimum distance between source 501 and surfaces 513, 514. The curvature of reflective surfaces 511, 512 may be of a constant radius or a variable radius and/or a radius that varies both in a vertical and horizontal direction.

The photocatalytic device may include enclosure 515 (e.g., housing 104 in FIG. 1) that protects and/or supports the components, including ultraviolet source 501, reflectors 508, 511, 512, and target structures 502, 503. Enclosure 515 may include ventilated or perforated sections 516, 517 to allow air (518) to flow through the device (e.g., inlet opening 105 and/or outlet opening 111 in FIG. 1). Additionally, reflectors 508 may be ventilated or perforated to allow air to flow through the device, thereby allowing for the distribution of hydro peroxides, hydroxyl ions, or other ions into a ventilation system or room.

FIG. 6 is a block diagram illustrating another photocatalytic device according to some embodiments. As illustrated in FIGS. 3-5, the reflectors in the photocatalytic device may be of a generally curved, convex shape. FIG. 6 illustrates an alternative reflector configuration in which bent reflectors 601-604 have a convex shape, but the reflectors have straight segments. The reflectors 601-604 serve the same purpose as reflectors 508, 511, 512 (FIG. 5) wherein ultraviolet light from source 605 is reflected against the surfaces of target structures 606, 607.

Straight reflectors 601-604 may be preferable to curved reflectors under certain manufacturing conditions, for example. The size, shape and angle of bent reflectors 601-604 are selected to optimize the uniform distribution of ultraviolet light across the surfaces of target structures 606, 607. It will be understood that other convex shapes may also be used for the reflectors in other embodiments. For example, reflector 604 has two segments and thus a single peak. In certain embodiments, however, reflector 604 (or any other of reflectors 601-604) may include two or more peaks (i.e., four or more straight segments), thus creating a "jagged profile." In some cases, such a jagged profile may include two or more peaks and valleys with different heights and/or angles that that cause the ultraviolet light to become even more evenly scattered and/or distributed across the surfaces of target structures 606, 607. In some cases, the different heights and/or angles of the two or more peaks and valleys may be selected using a random or pseudo-random sequence of numbers within one or more threshold value(s) (e.g., minimum height, maximum height, minimum angle, maximum angle, number of segments, etc.).

Similarly as above, the photocatalytic device may have an enclosure 608 with ventilated sections 609. Additionally, reflectors 601, 602 may be ventilated in order to improve airflow 610 through the photocatalytic device.

Although the invention(s) is/are described herein with reference to specific embodiments, various modifications and changes can be made without departing from the scope of the present invention(s), as set forth in the claims below. Accordingly, the specification and figures are to be regarded in an illustrative rather than a restrictive sense, and all such modifications are intended to be included within the scope of the present invention(s). Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements. The term "coupled" is defined as connected, although not necessarily directly, and not necessarily mechanically. The terms "a" and "an" are defined as one or more unless stated otherwise. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, device, or apparatus that "comprises," "has," "includes" or "contains" one or more elements possesses those one or more elements but is not limited to possessing only those one or more elements. Similarly, a method or process that "comprises," "has," "includes" or "contains" one or more operations possesses those one or more operations but is not limited to possessing only those one or more operations.

The invention claimed is:

1. A photocatalytic device, comprising:
a cylindrical housing having an inlet opening and an outlet opening;
one or more catalyst substrates disposed within the cylindrical housing and adapted to support a hydroxyl radical reaction with ultraviolet light and water vapor that results in hydro peroxides and hydroxyl ions, the one or more catalyst substrates comprising a hydrated multi-metallic catalyst having two or more elements selected from the group: Titanium dioxide, Platinum, Gold, Silver, Copper, Rhodium, Ruthenium, and Lanthanum;
an ultraviolet light source disposed within the cylindrical housing and adapted to provide the ultraviolet light to the one or more catalyst substrates; and
a fan disposed within the cylindrical housing and adapted to cause air to enter the cylindrical housing via the inlet opening, circulate through the one or more catalyst substrates within the cylindrical housing, and exit the cylindrical housing via the outlet opening.

2. The photocatalytic device of claim 1, wherein the hydrated multi-metallic catalyst further comprises one or more additional elements.

3. The photocatalytic device of claim 2, wherein the one or more additional elements comprise at least one of Carbon and Fluoride.

4. The photocatalytic device of claim 1, wherein the one or more catalyst substrates comprises a hydrated multi-metallic catalyst having four elements selected from the group: Titanium dioxide, Platinum, Gold, Silver, Copper, Rhodium, Ruthenium, Lanthanum, Carbon, and Fluoride.

5. The photocatalytic device of claim 1, wherein the one or more catalyst substrates comprises a hydrated quad-metallic catalyst having four elements selected from the group: Titanium dioxide, Platinum, Gold, Silver, Copper, Rhodium, Ruthenium, Lanthanum, Carbon, and Fluoride.

6. The photocatalytic device of claim 1, wherein the one or more catalyst substrates comprises a hydrated quintuple-metallic catalyst having five elements selected from the group: Titanium dioxide, Platinum, Gold, Silver, Copper, Rhodium, Ruthenium, Lanthanum, Carbon, and Fluoride.

7. The photocatalytic device of claim 6, wherein the one or more catalyst substrates comprise a cylindrical catalyst substrate.

8. The photocatalytic device of claim 1, wherein the one or more catalyst substrates comprises a hydrated sextuple-metallic catalyst having six elements selected from the group: Titanium dioxide, Platinum, Gold, Silver, Copper, Rhodium, Ruthenium, Lanthanum, Carbon, and Fluoride.

9. The photocatalytic device of claim 1, wherein the one or more catalyst substrates comprises a hydrated multi-metallic catalyst having at least five elements selected from the group: Titanium dioxide, Platinum, Gold, Silver, Copper, Rhodium, Ruthenium, Lanthanum, Carbon, and Fluoride.

10. The photocatalytic device of claim 1, further comprising:
a diffuser coupled to the cylindrical housing and adapted to spread the air exiting the cylindrical housing via the outlet opening.

11. The photocatalytic device of claim 1, wherein the photocatalytic device is configured to operate in an upright position.

12. The photocatalytic device of claim 1, wherein the photocatalytic device is configured to operate in a horizontal position when plugged into a wall socket power outlet.

13. The photocatalytic device of claim 1, further comprising:
one or more reflectors disposed within the cylindrical housing and positioned adjacent to the one or more catalyst substrates, the one or more reflectors having a shape configured to distribute reflected ultraviolet light from the ultraviolet light source across a surface of the one or more catalyst substrates.

14. The photocatalytic device of claim 1, wherein the photocatalytic device is configured to selectively operate in an upright position using a cord extending from the housing and plugged into a wall socket power outlet, and selectively operate in a horizontal position disposed against a wall using a plug extending from the housing plugged into a wall socket power outlet, the wall socket power outlet supporting the photocatalytic device.

15. A method, comprising:
causing air to enter a cylindrical housing of a photocatalytic device via an inlet opening, circulate through one or more catalyst substrates within the cylindrical housing, and exit the cylindrical housing via an outlet opening, the one or more catalyst substrates adapted to support a hydroxyl radical reaction with ultraviolet light and water vapor that results in hydro peroxides and hydroxyl ions within the photocatalytic device, the one or more catalyst substrates comprising a hydrated multi-metallic catalyst having two or more elements selected from the group: Titanium dioxide, Platinum, Gold, Silver, Copper, Rhodium, Ruthenium, and Lanthanum the ultraviolet light provided by an ultraviolet light source disposed within the cylindrical housing.

16. The method of claim 15, wherein the one or more catalyst substrates comprises a hydrated multi-metallic catalyst having five or more elements selected from the group: Titanium dioxide, Platinum, Gold, Silver, Copper, Rhodium, Ruthenium, Lanthanum, Carbon, and Fluoride.

17. The method of claim 15, further comprising:
reflecting the ultraviolet light by one or more convex reflectors disposed within the cylindrical housing and positioned adjacent to the one or more catalyst substrates.

18. The method of claim 17, wherein a shape of the one or more convex reflectors is configured to minimize a distance between the ultraviolet light source and a near surface of the one or more catalyst substrates.

19. The method of claim 17, wherein a shape of the one or more convex reflectors is configured to minimize a distance between the ultraviolet light source and a far surface of the one or more catalyst substrates.

20. A photocatalytic device, comprising:
a cylindrical housing having an inlet opening and an outlet opening;
one or more catalyst substrates disposed within the cylindrical housing and adapted to support a hydroxyl radical reaction with ultraviolet light and water vapor that results in hydro peroxides and hydroxyl ions, the one or more catalyst substrates comprising a hydrated multi-metallic catalyst having two or more elements selected from the group: Titanium dioxide, Platinum, Gold, Silver, Copper, Rhodium, Ruthenium, Lanthanum, Carbon and Fluoride;
an ultraviolet light source disposed within the cylindrical housing and adapted to provide the ultraviolet light to the one or more catalyst substrates; and
a fan disposed within the cylindrical housing and adapted to cause air to enter the cylindrical housing via the inlet opening, circulate through the one or more catalyst substrates within the cylindrical housing, and exit the cylindrical housing via the outlet opening.

* * * * *